US006424867B1

United States Patent
Snell et al.

(10) Patent No.: US 6,424,867 B1
(45) Date of Patent: Jul. 23, 2002

(54) SECURE TELEMETRY SYSTEM AND METHOD FOR AN IMPLANTABLE CARDIAC STIMULATION DEVICE

(75) Inventors: Jeffery D. Snell, Oak Park; Laurence S. Sloman, West Hollywood, both of CA (US)

(73) Assignee: Pacesetter, Inc., Sylmar, CA (US)

(*) Notice: Subject to any disclaimer, the term of this patent is extended or adjusted under 35 U.S.C. 154(b) by 0 days.

(21) Appl. No.: 09/410,517

(22) Filed: Sep. 30, 1999

(51) Int. Cl.[7] .................................................. A61N 1/37
(52) U.S. Cl. ............................. 607/31; 607/32; 607/60
(58) Field of Search .............................. 607/30–32, 59, 607/60; 128/903

(56) References Cited

U.S. PATENT DOCUMENTS

| 4,712,555 A | 12/1987 | Thornander et al. .. 128/419 PG |
| 4,788,980 A | 12/1988 | Mann et al. .......... 128/419 PG |
| 4,875,483 A | 10/1989 | Vollmann et al. ............ 128/419 |
| 4,940,052 A | 7/1990 | Mann et al. .......... 128/419 PG |
| 4,944,298 A | 7/1990 | Sholder ...................... 128/419 |
| 5,720,771 A | 2/1998 | Snell ............................. 607/60 |
| 5,725,559 A | 3/1998 | Alt et al. ........................ 607/5 |
| 5,843,138 A | 12/1998 | Evers et al. ................... 607/30 |
| 5,843,139 A | * 12/1998 | Goedeke et al. .............. 607/32 |

* cited by examiner

Primary Examiner—Jeffrey R. Jastrzab

(57) ABSTRACT

An implantable cardiac stimulation device establishes communication with at least first and second external devices which communicate using first and second communication protocols, respectively, and wherein the first and second protocols are different. The implantable device includes a pulse generator configured to generate stimulation pulses and a telemetry circuit arranged to establish communication with the first and second external devices according to the first and second communication protocols, respectively. A control circuit coupled to the telemetry circuit and the pulse generator detects the first and second external devices based upon the protocol used in establishing communication to provide a first response when the first external device is detected and a second response when the second external device is detected.

45 Claims, 3 Drawing Sheets

SECURE TELEMETRY SYSTEM AND METHOD FOR AN IMPLANTABLE CARDIAC STIMULATION DEVICE

FIELD OF THE INVENTION

The present invention is generally directed to an implantable stimulation device. The present invention is more particularly directed to such a device which provides telemetry communication with various different types of external devices and which is capable of detecting the type of external device with which is communicated and providing a corresponding appropriate response.

BACKGROUND OF THE INVENTION

Implantable cardiac stimulation devices are well known in the art. They include implantable pacemakers which provide stimulation pulses to a heart to cause a heart, which would normally or otherwise beat too slowly or at an irregular rate, to beat at a controlled normal rate. They also include defibrillators which detect when the atria and/or the ventricles of the heart are in fibrillation and apply cardioverting or defibrillating electrical energy to the heart to restore the heart to a normal rhythm. Implantable cardiac stimulation devices may also include the combined functionalities of a pacemaker and a defibrillator.

Implantable cardiac stimulation devices have become extremely sophisticated. As is well known, they are able to provide therapy to a heart based upon numerous different programmable parameters. Such programmable parameters may, for example, control therapy modality, pacing rates, refractory periods, pacing and defibrillating pulse energies, detection sensitivities, and the like.

Programmable parameter selection is normally achieved with an external programmer which establishes a communication channel via telemetry with the implanted device. To that end, the implantable devices include a telemetry circuit including a transmitter for transmitting device related information and electrograms to the external programmer and a receiver for receiving information, such as programmable parameter commands, from the external programmer. As a result of such external programmability, the implanted devices may be reprogrammed by the physician to continually adapt the device to a patient's changing condition.

More recently, with improvements in increased memory storage capacity, the implantable cardiac storage devices are now also seen as being capable of storing cardiac data which could not be previously stored. Such data may include, for example, device history data, cardiac data including stored electrograms to be used at follow-up visits, or cardiac data useful in diagnosing cardiac conditions other than those currently being treated by the implanted device.

As can thus be seen, the telemetry channel may be used to both read data from the implanted device and to send data into the device. Some of the data that is sent into the device is information that is passive and simply recorded in memory, to be read back at a later time. Other data that is sent into the device is active and causes changes in the behavior or operation of the device. Some of the active data, when sent to the device, will cause operational changes which do not impact the therapy provided to the patient. Such data may include diagnostic data recording modes or real time data transmission channel selections. Active data sent to the implanted device does impact on the therapy received by the patient. Such data may include parameters such as pacing rate, mode, and rate responsive slope, for example. In some other cases, reading of data from an implanted device can cause active changes in the therapy being delivered to the patient. For example, temporary changes in pacing rate and modality may be required for reading measured data while more permanent changes are also possible results of reading data from a device.

Hence, there are a number of potential uses for the telemetry interface which can benefit from the ability to read data from an implanted device and to control active behavior of the device without affecting the therapy delivered to the patient. To ensure that the health and safety of the patient are maintained at all times, it is particularly desirable, if not necessary, to require that the possibility of affecting the therapy delivered be reduced to effectively zero. Examples of applications that could utilize this function are transtelephonic monitoring devices, patient activated data recording device, Holter-style recording instruments, stand-alone patient monitoring devices, or patient monitoring devices linked to a central station.

Unfortunately, these applications cannot use the same RF telemetry communications protocol as is typically used by programmers to communicate with and control the implanted device. This is because the potential exists for inadvertently affecting the therapy delivered by the device when errors enter the communications link, either as noise or interference in the RF link or by errors in the operation of the non-programming monitoring devices.

Prior systems have failed to provide adequate security to permit partial programming or non-programming devices to communicate with an implantable device. For example, systems are known wherein partial programming or non-programming external devices communicate with implanted devices using the same protocol as the devices full-featured programmer. These systems simply rely on the partial programming or non-programming device having limited or no programming ability. However, because they use the same protocol as the devices programmer, noise or interference with the communication link could cause the programmable parameters of the implanted device and thus the therapy delivered by the implanted device to be inadvertently affected by communication with a partial programming or non-programming device.

Other systems fail to recognize that partial programming or non-programming devices may be in communication with an implanted device. For example, U.S. Pat. No. 4,875,483 describes a system wherein an implantable stimulator uses a program access code to control who may change the programming of the device. Identification of an external device type by an implantable device is not contemplated.

U.S. Pat. No. 5,725,559 describes a system wherein an implantable stimulator uses codes to determine the current programming of the implanted device and the level of therapy the device is authorized to provide. While the system permits some level of personnel to provide maintenance type work on the device using the programmer, only a physician can upgrade the therapies given to the patient. However, the concept of the implanted device communicating with different types of external devices other than a programmer is not addressed.

U.S. Pat. No. 5,843,138 describes a system wherein a programmer is capable of programming the implanted device in a conventional way and also downloading new control software to the implanted device, subject to predetermined system conditions. Upon interrogating the implanted device, the programmer determines whether the device is of the type which it is able to modify. Again, the described implanted device fails to respond to the need of being capable of different types of external devices and identifying the type of external device with which it is communicating for the purpose of providing an appropriate response.

Therefore, there is a need in the art for a new and improved implantable cardiac stimulation device which may communicate with various types of external devices including programmers which may change the operation of the implantable device and other external devices such as monitors which are intended to make minor modifications in the device operation and/or read data from the implanted device. More particularly, there is a need in the art for an implantable cardiac stimulation device which is capable of communicating with a plurality of different external devices, detecting the type of external device in which it is communicating, and then providing a suitable appropriate response to the external device.

SUMMARY OF THE INVENTION

The present invention is directed to an implantable cardiac stimulation device and method which provides secure communication between the implantable device and a plurality of different types of external devices such as programmers, intended to change therapy parameters of the implantable device, and monitors, intended to monitor device operation or patient condition. To that end, the implantable cardiac stimulation device detects they type of external device, of a plurality of different external devices, with which it is communicating for providing an appropriate response depending on the type of external device detected. When the external device is a programmer, an appropriate response includes permitting access to a portion or all of the programmable parameters of the device. When the external device is a monitor, not intended to program the device, an appropriate response includes locking out access to the programmable parameters while permitting access to readable memory portions containing, for example, data or other information concerning device operation or the patient's condition.

In accordance with the present invention, the implantable cardiac stimulation device includes a telemetry circuit which establishes communication with the external devices using, for each external device; a respective different communication protocol. A control circuit of the implantable device detects the external device based upon the communication protocol being used to support the communication.

The different protocols may be different encoding schemes, different data transmission rates, or different required access codes including access code verification or modification during the communication. At least one protocol may further require serial access codes for access to programmable parameters. Still further, each of the serial access codes may be different.

To ensure that a non-programmer does not gain access to the programmable parameters following communication with a programmer, the telemetry circuit may be deactivated upon completion of the communication with a programmer. The deactivation may be provided by a timer which automatically times out after completion of the communication.

BRIEF DESCRIPTION OF THE DRAWINGS

The above and other aspects, features, and advantages of the present invention will be more apparent from the following more particular description thereof presented in conjunction with the following drawings wherein.

DETAILED DESCRIPTION OF THE PREFERRED EMBODIMENTS

The following description is of the best mode presenting contemplated for carrying out the invention. This description is not to be taken in a limiting sense, but is made merely for the purpose of describing the general principles of the invention. The scope of the invention should be determined with reference to the claims.

As indicated above, the present invention may be used with various types of implantable stimulation devices, including an implantable pacemaker configured to treat bradycardia and/or tachycardia, an implantable cardioverter-defibrillator (ICD), or a combination thereof.

To better understand the invention, it will first be helpful to have an understanding of the basic functions performed by the implantable stimulation device with which the invention is used, for example, a dual-chamber pacemaker. While a dual-chamber device has been chosen, this is for teaching purposes only. It is recognized that the present invention could be implemented into an ICD device or a single-chamber pacemaker, that one of skill in the art could readily adapt the dual-chamber device shown in FIG. 1 to perform single-chamber functionality, and a single-chamber device or an ICD device is within the spirit of the invention.

Figure 1:
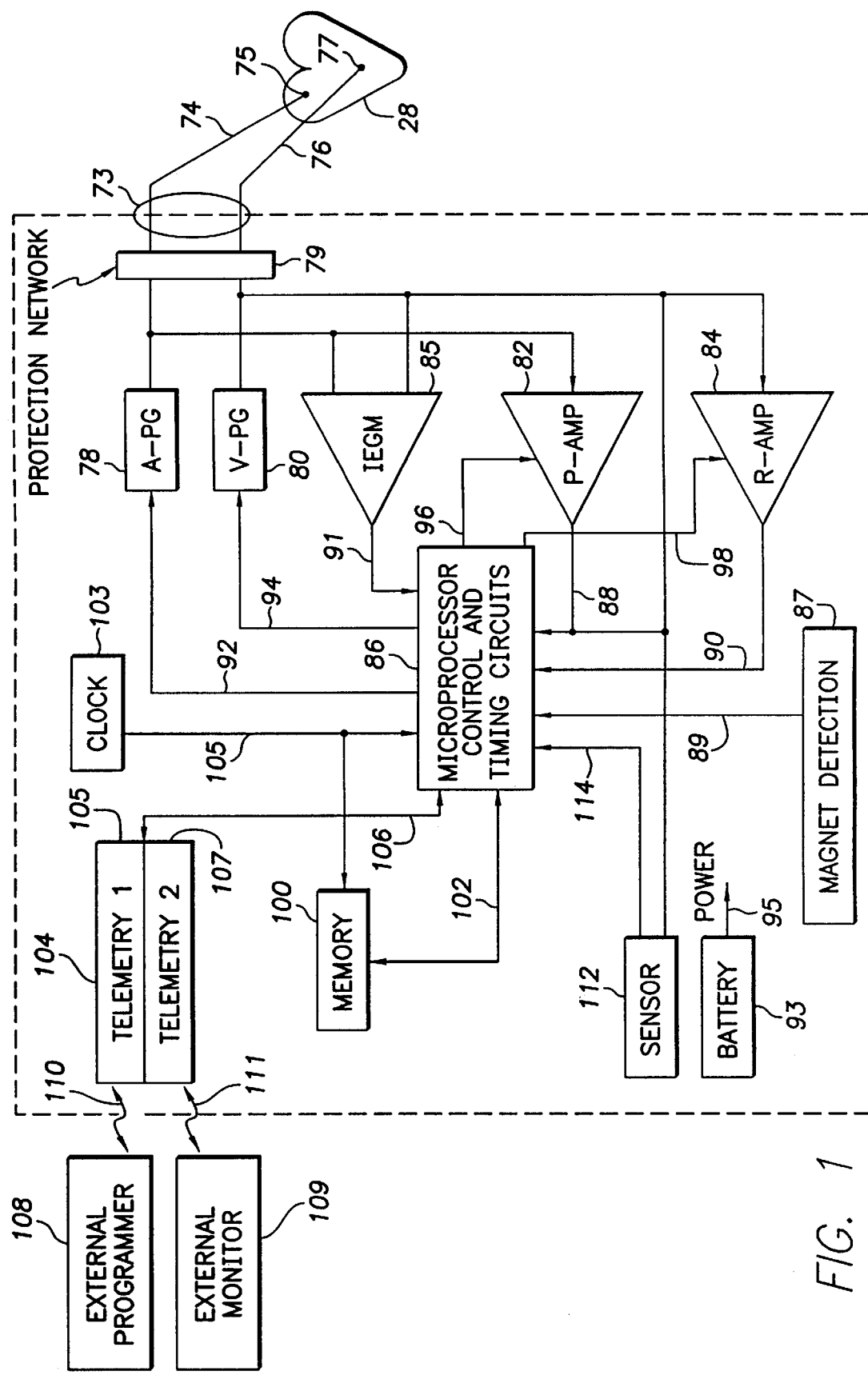
FIG. 1 shows a functional block diagram of an implantable dual-chamber pacemaker, which represents one type of implantable cardiac stimulation device with which the invention may be used.

In FIG. 1, a simplified block diagram of the circuitry needed for a dual-chamber pacemaker 70 is illustrated. The pacemaker 70 is coupled to a heart 28 by way of leads 74 and 76, the lead 74 having an electrode 75 that is in contact with one of the atria of the heart, and the lead 76 having an electrode 77 that is in contact with one of the ventricles of heart. The leads 74 and 76 are electrically and physically connected to the pacemaker 70 through a connector 73 that forms an integral part of the housing wherein the circuits of the pacemaker are housed.

The connector 73 is electrically connected to a protection network 79, which network 79 electrically protects the circuits within the pacemaker 70 from excessive shocks or voltages that could appear on the electrodes 75 and/or 77 in the event such electrodes were to come in contact with a high voltage signal, for example, from a defibrillation shock.

The leads 74 and 76 carry stimulating pulses to the electrodes 75 and 77 from an atrial pulse generator (A-PG) 78 and a ventricular pulse generator (V-PG) 80, respectively. Further electrical signals from the atria are carried from the electrode 75 through the lead 74 to the input terminal of an atrial channel sense amplifier (P-AMP) 82; and electrical signals from the ventricles are carried from the electrode 77, through the lead 76, to the input terminal of the ventricular channel sense amplifier (R-AMP) 84. Similarly, electrical signals from both the atria and ventricles are applied to the inputs of an IEGM (intracardiac electrogram) amplifier 85. The amplifier 85 is typically configured to detect an evoked response from the heart 28 in response to an applied stimulus, thereby aiding in the detection of "capture." Capture occurs when an electrical stimulus applied to the heart is of sufficient energy to depolarize the cardiac tissue, thereby causing the heart muscle to contract, or in other words, causing the heart to beat. Capture does not occur when an electrical stimulus applied to the heart is of insufficient energy to depolarize the cardiac tissue.

The dual-chamber pacemaker 70 is controlled by a control circuit or system 86 that typically includes a microprocessor programmed to carry out control and timing functions. The control system 86 receives the output signals from the atrial amplifier 82 over signal line 88. Similarly, the control system 86 receives the output signals from the ventricular amplifier 84 over signal line 90, and the other signals from the IEGM amplifier 85 over signal line 91. These output signals are generated each time that a P-wave or an R-wave, or an evoked response is sensed within the heart 28. The control system 86 also generates trigger signals that are sent to the atrial pulse generator 78 and the ventricular pulse generator 80 over lines 92 and 94, respectively. These trigger signals are generated each time that a stimulation pulse is to be generated by the respective pulse generator 78 or 80. The atrial trigger signal is referred to simply as the "A-trigger" and the ventricular trigger signal is referred to as the "V-trigger."

During the time that either an A-pulse or V-pulse is being delivered to the heart, the corresponding amplifier, P-AMP 82 and/or R-AMP 84, is typically disabled by way of a blanking signal presented to these amplifiers from the control system over signal lines 96 and 98, respectively. This blanking action prevents the amplifiers 82 and 84 from becoming saturated from the relatively large stimulation pulses that are present at their input terminals during this time. This blanking action also helps prevent residual electrical signals present in the muscle tissue as a result of the pacemaker stimulation from being interpreted as P-waves or R-waves.

As shown in FIG. 1, the pacemaker 70 further includes a memory circuit 100 that is coupled to the control system 86 over a suitable data-address bus 102. This memory circuit 100 allows certain control parameters, used by the control system 86 in controlling the operation of the pacemaker, to be programmably stored and modified by an external programmer 108, as required, in order to customize the pacemaker's operation to suit the needs of a particular patient. Further, data sensed during the operation of the pacemaker may be stored in the memory 100 for later retrieval and analysis by either the programmer 108 or an external monitor 109.

The memory 100 of the pacemaker 70 may take many forms, and may be subdivided into as many different memory blocks, portions, or sections as needed in order to allow desired data and control information to be stored. A feature of the present invention, in some embodiments thereof, is the ability to detect the type of external device communicating with the implantable device 70 and, depending on the type of device detected, provide an appropriate response. If the device 70 is communicating programmer 108, for example, an appropriate response would include permitting access to the portions of memory 100 which store both readable data and programmable parameters. If, on the other hand, the device 70 is communicating with external monitor 109, not intended to program the device 70, an appropriate response may include precluding access to the programmable parameters while permitting access to those readable data portions which the monitor is intended to read. Still further, if the monitor requires temporary modification of some programmable parameters to permit the intended data to be generated and stored, an appropriate response may be to permit access to only those programmable parameters required for temporary modification to permit the intended data to be generated.

The pacemaker 70 further includes a telemetry/communications circuit 104. In accordance with the present invention, the telemetry circuit 104 includes a first telemetry circuit 105 for communicating with the external programmer 108 in accordance with a first protocol and a second telemetry circuit 107 for communicating with the external monitor 109 in accordance with a second and different protocol. The telemetry circuit 104 is connected to the control system 86 by way of a suitable command/data bus 106. The control system detects the type of external device communicating with the implantable device 70 and causes an appropriate response of the type discussed above. The telemetry circuits 105 and 107 may be selectively coupled to their respective external devices by means of appropriate communication links 110 and 111, respectively, which communication links 110 and 111 may be any suitable electromagnetic link, such as an RF (radio frequency) channel, a magnetic link, an inductive link, an optical link, and the like. The external devices 108 and 109 may use the same type of link or different types of links with the different types of links being the different protocols. Advantageously, through the external devices 108 and 109 and the communication links 110 and 111 i desired commands may be sent to the control system 86. The control system 86 then responds according to the type of external device initiating the commands based upon the protocol used to establish the communication. Through communication links 110 and 111 the external devices 108 and 109 may send commands to be remotely received by the telemetry circuits 105 and 107. Similarly, data initially sensed through the leads 74 or 76, and processed by the microprocessor control circuit 86, or other data measured within or by the pacemaker 70, may be stored and uploaded along with command confirmations, such as programmable parameter modification confirmations, to the external devices 108 and 109. In this manner, non-invasive communications can be established with the implanted pacemaker 70 from the remote, non-implanted, external devices 108 and 109.

Although the telemetry circuits 105 and 107 are individually shown in FIG. 1, it will be understood by those skilled in the art that they are represented individually to generically illustrate that each is capable of communicating with its respective external device using respectively different protocols. Hence, it should be understood that the telemetry circuits 105 and 107 may be totally separate as illustrated or share the same circuit hardware while utilizing different protocol software to support the differing protocols.

A clock circuit 103 directs an appropriate clock signal to the control system 86, as well as to other needed circuits throughout the pacemaker 70 by way of clock bus 105. Additionally, the pacemaker 70 includes a battery 93. It provides operating power to all of the circuits of the pacemaker 70 via a power signal line 95.

It is noted that the pacemaker 70 in FIG. 1 is referred to as a dual-chamber pacemaker because it interfaces with both the atria and ventricles of the heart. Those portions of the pacemaker 70 that interface with the atria, for example the lead 74, the sense amplifier 82, the atrial pulse generator 78, and corresponding portions of the control system 86, are commonly referred to as the "atrial channel." Similarly, those portions of the pacemaker 70 that interface with the ventricles, for example the lead 76, the R-wave sense amplifier 84, the ventricular pulse generator 80, and corresponding portions of the control system 86, are commonly referred to as the "ventricular channel."

As need for certain applications, the pacemaker 70 may further include at least one sensor 112 that is connected to the control system 86 of the pacemaker 70 over a suitable connection line 114. While this sensor 112 is illustrated in FIG. 1 as being included within the pacemaker 70, it is to be understood that the sensor may also be external to the pacemaker 70, yet still be implemented within or carried by the patient. A common type of sensor is an activity sensor, such as a piezoelectric crystal that is mounted to the case of the pacemaker. Other types of sensor are also known, such as sensors that sense the oxygen content of the blood, respiration rate, pH of blood, body motion, and the like. The type of sensor used is not critical to the present invention. Any sensor or combination of sensors capable of sensing a physiological or physical parameter relatable to the rate at which the heart should be beating and/or relatable to whether a tachyarrhythmia is likely to soon occur, can be used. Such sensors are commonly used with "rate-responsive" pacemakers in order to adjust the rate of the pacemaker in a manner that tracks the physiological or metabolic needs of the patient.

The pacemaker 70 further includes magnet detection circuitry 87, coupled to the control system 86 over signal line 89. It is the purpose of the magnet detection circuitry 87 to detect when a magnet is placed over the pacemaker, which magnet may be used by a physician or other medical personnel to perform various reset functions of the pacemaker 70 and/or to signal the control system 86 that an external device such as programmer 108 or external monitor 109 is in place to receive data from, or send data to, the pacemaker memory 100 or control system 86 through the telemetry communication circuits 105 or 107.

The memory circuit 100, and the circuits utilized in the atrial and ventricular channels may all be of common design as is known in the pacing art. The present invention is not concerned with the details of the circuitry utilized for each of these pacing elements. Rather, it is concerned with the manner in which all of these pacing elements cooperate with each other in order to provide a particular pacing mode of operation. Such cooperation is controlled by the control system 86.

The control system 86 may be realized using a variety of different techniques and/or circuits. The preferred type of control system 86 is a microprocessor-based control system. It is noted, however, that the control system 86 could also be realized using a state machine. Indeed, any type of control circuit or system could be employed for the control system 86. So long as the control system 86 controls the operation of the pacemaker (or other medical device) so that the desired functions are achieved as set forth herein, it matters little what type of control system is used. Those of skill in the implantable medical device art, given the teachings presented herein, should thus be able to fashion numerous different types of control systems or circuits that achieve the desired device control Representative of the types of control systems that may be used with the invention is the microprocessor-based control system described in U.S. Pat. No. 4,940,052 entitled MICROPROCESSOR CONTROLLED RATE-RESPONSIVE PACEMAKER HAVING AUTOMATIC RATE RESPONSE THRESHOLD ADJUSTMENT. Reference is also made to U.S. Pat. Nos. 4,712,555 and 4,944,298, wherein a state-machine type of operation for a pacemaker is described; and U.S. Pat. No. 4,788,980, wherein the various timing intervals used within the pacemaker and their inter-relationship are more thoroughly described. The '052, '555, '298, and '980 patents are incorporated herein by reference.

As previously mentioned, a feature of the present invention is the ability to detect the type of external device communicating with the implantable device 70 based upon the protocol used to support the communication and, depending on the type of device detected, provide an appropriate response. Reference will now be made to FIGS. 2–9 which illustrate various embodiments and manners of implementing the present invention. Preliminarily, the telemetry circuit functional block diagrams of FIGS. 2–6 and 9 illustrate certain protocol defining functionality to be resident in the telemetry circuits. While this may be a preferred implementation, it will be understood by those skilled in the art that some or all of the illustrated protocol defining functionality could alternatively reside within the control circuit 86 instead. Also, in these figures, individual telemetry circuits supporting different telemetry protocols are separately illustrated. However, as previously mentioned, the telemetry circuits may share telemetry circuitry hardware and instead implement the differing telemetry protocols through software or other separate control.

Figure 2:
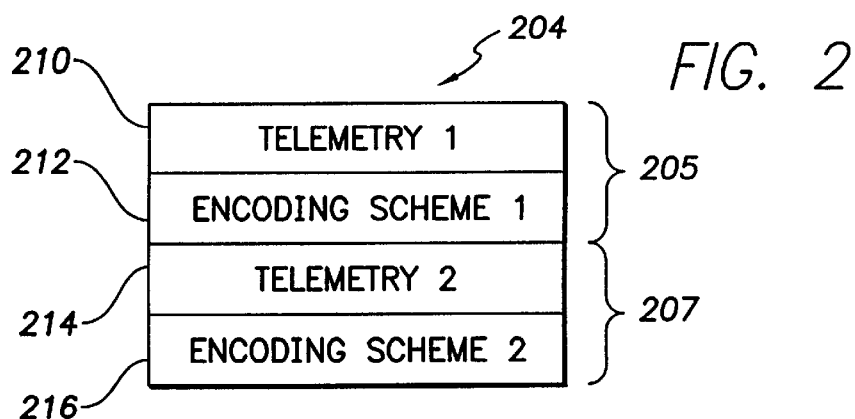
FIG. 2 shows a functional block diagram of a telemetry circuit which may be used in the device of FIG. 1 wherein the different protocols are different encoding schemes.

Referring now to FIG. 2, it shows a telemetry circuit 204 which may be used in the pacemaker 70 of FIG. 1 in accordance with a first embodiment of the present invention. The telemetry circuit 204 includes a first telemetry circuit 205 for communicating with, for example, the external programmer 108 and a second telemetry circuit 207 for communicating with, for example, the external monitor 109. The first circuit 205 includes telemetry circuit hardware 210 which may include a transmitter and a receiver and a first encoding scheme 212 corresponding to the encoding scheme of the programmer 108. The second circuit 207 similarly includes telemetry circuit hardware 214 which may also include a transmitter and a receiver and a second encoding scheme 216 corresponding to the encoding scheme of the external monitor 109.

The first and second encoding schemes are different resulting in, first and second communication protocols, respectively. For example, one of the encoding schemes may be a pulse position modulation scheme while the other encoding scheme is a phase shift encoding scheme. As a further example, one encoding scheme may use complete or partial digital inversion while the other does not. Still further, one encoding scheme may utilize a cyclical redundancy code while the other encoding scheme uses any of the other encoding schemes mentioned above.

The differing encoding schemes and thus protocols of the telemetry circuit 204 permit the control circuit 86 to detect the type of external device communicating with the implantable device 70. When the external programmer is communicating with telemetry circuit 205, the control circuit 86 may provide access to the programmable parameters stored in the memory 100 along with the readable data. However, if the external monitor is communicating with telemetry circuit 207, the control circuit 86, may provide access to only the readable data stored in the memory 100 while blocking access to the programmable parameters. Hence, by virtue of the respective different protocols for communication with the different external devices, the type of external device communicating with the implantable device may be detected to facilitate an appropriate response while also providing enhanced security to assure that the implantable device will not inadvertently mistake one external device for another. This precludes the implantable device, for example, from providing access of programmable parameters to an external monitor, for example.

Figure 3:
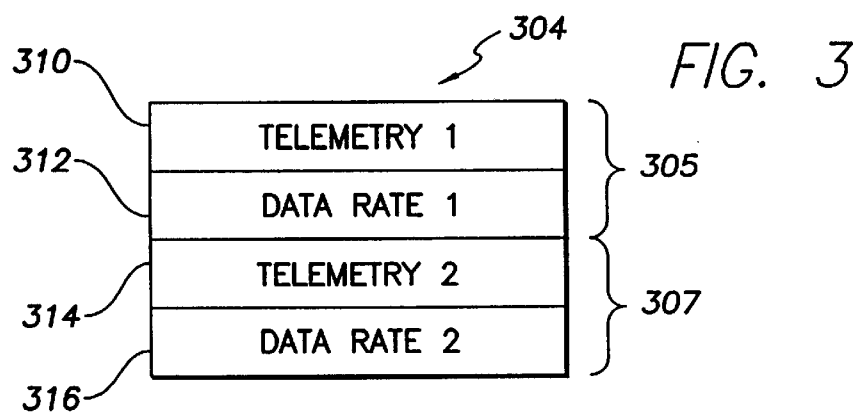
FIG. 3 shows a functional block diagram of another telemetry circuit which may be used in the device of FIG. 1 wherein the different protocols are different data transmission rates.

FIG. 3 shows another telemetry circuit 304 which may be used in the pacemaker of FIG. 1 in accordance with another embodiment of the present invention. Again, the telemetry circuit 304 includes a first telemetry circuit 305 and a second telemetry circuit 307. The telemetry circuits include telemetry hardware 310 and 314, each including a transmitter and a receiver. The telemetry circuits 305 and 307 implement different respective protocols in the form of different data transmission rates under control of data rate controls 312 and 316, respectively. The different transmission rates enable external device identification to facilitate appropriate responses while providing required security.

Figure 4:
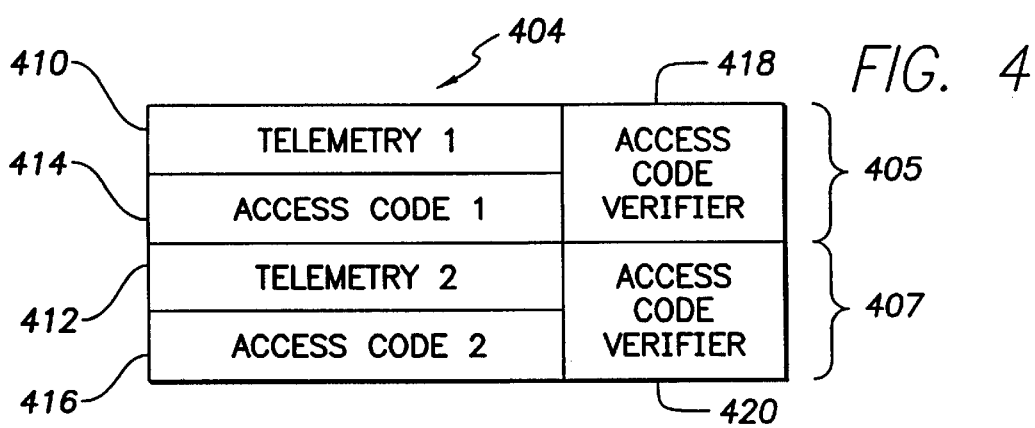
FIG. 4 shows a functional block diagram of a further telemetry circuit which may be used in the device of FIG. 1 wherein the different protocols include different access codes and access code verification.

Referring now to FIG. 4, it illustrates still another telemetry circuit 404 embodying further aspects of the present invention. Here the telemetry circuit 404 includes a first telemetry circuit 405 and a second telemetry circuit 407. The first telemetry circuit 405 includes telemetry circuit hardware 410 including a transmitter and a receiver. The second telemetry circuit 404 also includes telemetry hardware 412 including a transmitter and a receiver. The telemetry circuits 405 and 407 implement different respective protocols by requiring different access codes to establish communication with respective different external devices. To that end, the first telemetry circuit 405 includes a first access code control 414 while the second telemetry circuit 407 includes a second access code control 416.

In use, for communication to be established with an external programmer, for example, the external programmer would provide the first access code for communication with the first telemetry circuit 405. The external monitor, on the other hand, would be required to provide a second and different access code to be decoded by the second access code control 416 for communicating with the second telemetry circuit 407. To ensure that there isn't an inadvertent mistake in access code identification, each of the telemetry circuits 405 and 407 includes an access code verifier 418 and 420. The access code verifiers may be utilized to verify the access codes used by the respective telemetry circuits during a communication with an external device. As a communication with external device will most likely encompass a series of transmissions, the access code verifiers may preferably verify the respective access codes between each transmission of the external device to which its respective telemetry circuit is communicating.

As a result, the different access codes enable identification of the external device with which the implantable device is communicating. The different access codes and the access code verifiers provide security to assure that appropriate responses are provided and that a non-programming external device is not given access to programmable parameters of the implanted device.

Figure 5:
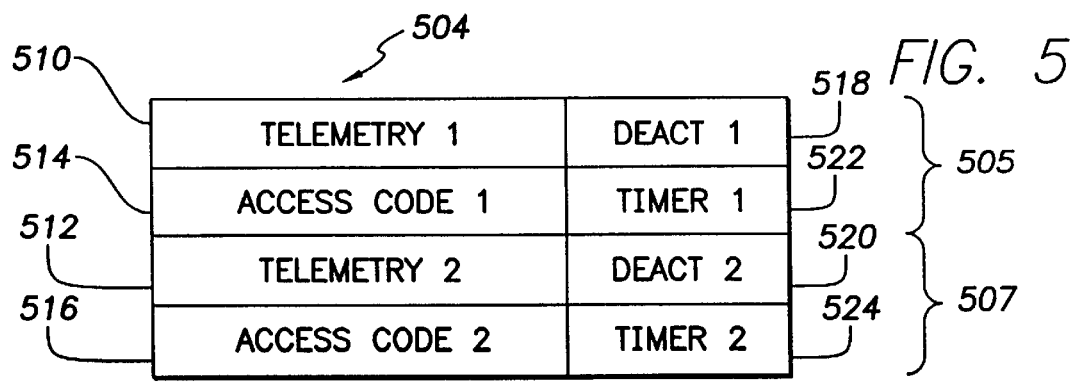
FIG. 5 shows a functional block diagram of another telemetry circuit which may be used in the device of FIG. 1 wherein the different protocols include different access codes and telemetry deactivation.

FIG. 5 shows a similar telemetry circuit 504 in that it includes a first telemetry circuit 505 and a second telemetry circuit 507 wherein, in addition to the telemetry circuit hardware 510 and 512, respectively, the telemetry circuits implement respective different protocols by requiring respective different access codes under control of access code controls 514 and 516, respectively. The operation of the telemetry circuit 504 in that regard is the same as the telemetry circuit 404 of FIG. 4.

In contrast to the telemetry circuit 404 of FIG. 4, each of the first and second telemetry circuits 505 and 507 includes a deactivation circuit 518 and 520, respectively. The first deactivation circuit 518 includes a timer 522 and the second deactivation circuit includes a second timer 524. The deactivation circuits deactivate the communications channel of its respective telemetry circuit by deactivating its telemetry circuit following communication with its respective external device. The timers 522 and 524 may be utilized for automatically timing a timeout so that the telemetry circuits 505 and 507 are deactivated a predetermined time after completion of communication with its external device. This assures that if, for example, a programmer has completed communication with the implanted device, an external monitor is unable to gain access to the programmable parameters by virtue of the communication channel being deactivated.

Figure 6:
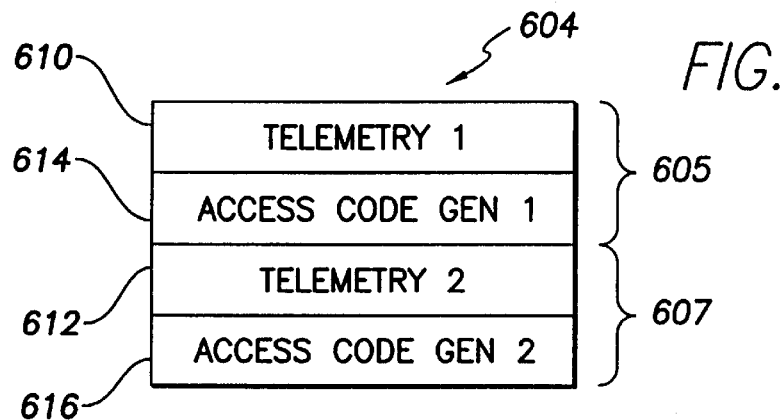
FIG. 6 shows a functional block diagram of another telemetry circuit which may be used in the device of FIG. 1 wherein the different protocols include different access codes which are changed or modified during communication.
Figure 7:
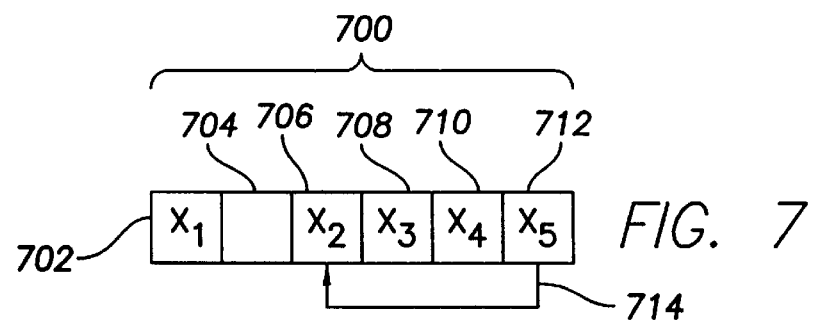
FIG. 7 is a general representation of an access code and a manner of modifying the access code during communication.

FIG. 6 shows another telemetry circuit 604 embodying still further aspects of the present invention. The telemetry circuit 604 includes a first telemetry circuit 605 and a second telemetry circuit 607. The first and second telemetry circuits 605 and 607 each includes first and second telemetry hardware 610 and 612, respectively, each including a transmitter and a receiver. The first and second telemetry circuits 605 and 607 implement different protocols by requiring different respective access codes which, during transmission with their respective external devices, are changed or modified. To that end, the first telemetry circuit 605 includes a first access code generator 614 the second telemetry circuit 607 includes a second access code generator 616. Preferably, the access codes are changed or modified between each transmission. The access codes may be modified in accordance with a pseudorandom-type generator in a manner as illustrated in FIG. 7. FIG. 7 illustrates an illustrative access code 700. The access code 700 includes six spaces wherein five of the six spaces contain a numerical value represented by a binary number. The first space 702($X_1$) may be a constant and depend on the type of external device. For example, the first digit 702 for an external programmer may always be a "5" while the first space 702 for an external monitor may be a "6." After the first space 702, there is a blank space 704 which is then followed by four consecutive spaces 706, 708, 710 and 712. As will be noted by the arrow 714, the access code 700 may be modified between transmissions by shifting the numerical value of the last space 712 to the third space 706 and then shifting the other numerical values to the right by one space. As the foregoing will be known by both the implantable device and the external device to which it is intended to communicate, even though the access code is modified between transmissions, the access code to which the implantable device will be looking at any one time will be known by the external device to which it is intended to communicate. However, other external devices will not have privy to the access code at any one time and will be precluded from evoking any response other than the response to which it is intended.

Figure 8:
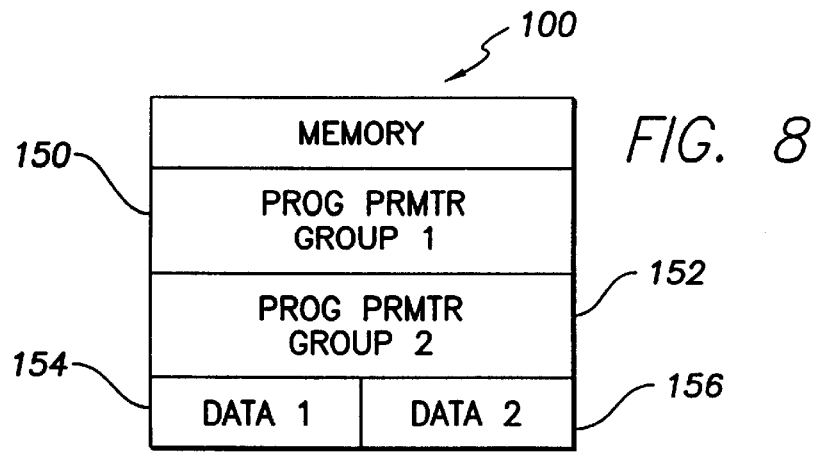
FIG. 8 shows a functional block diagram of the memory of the implantable cardiac stimulation device of FIG. 1 including first and second programmable parameter portions and first and second data portions.

FIG. 8 shows a functional block diagram of the memory 100 and a manner in which it may be portioned for storing program parameters and readable data. Here it will be seen that the memory includes a first program parameter portion 150 for storing a first group of programmable parameters and a second memory portion 152 for storing a second group of programmable parameters. The memory 100 also includes a first data portion 154 for storing a first group of data and a second data portion 156 for storing a second group of data. When a programmer establishes communication with the implantable device, a suitable response may be the access of both program parameter portions 150 and 152 to the programmer along with access to data portions 154 and 156. However, when the implantable device is communicating with an external monitor, an appropriate response may be the blocking out of the programmable parameter portions 150 and 152 while permitting access to one or both of the readable data portions 154 and 156. In those instances where an external monitor requires temporary modification of therapy programmable parameters, an appropriate response may be permitting access to one of the program groups 150 or 152 while precluding access to the other on a temporary basis to permit the required data to be generated. Hence, by partitioning the memory 100 and providing selective access by the control circuit 86 responsive to the type of external device communicating with the implantable device based upon the protocol utilized, an appropriate response can be generated to assure all of the required functionality is provided to the external device without providing memory portions which would be inappropriate.

Figure 9:
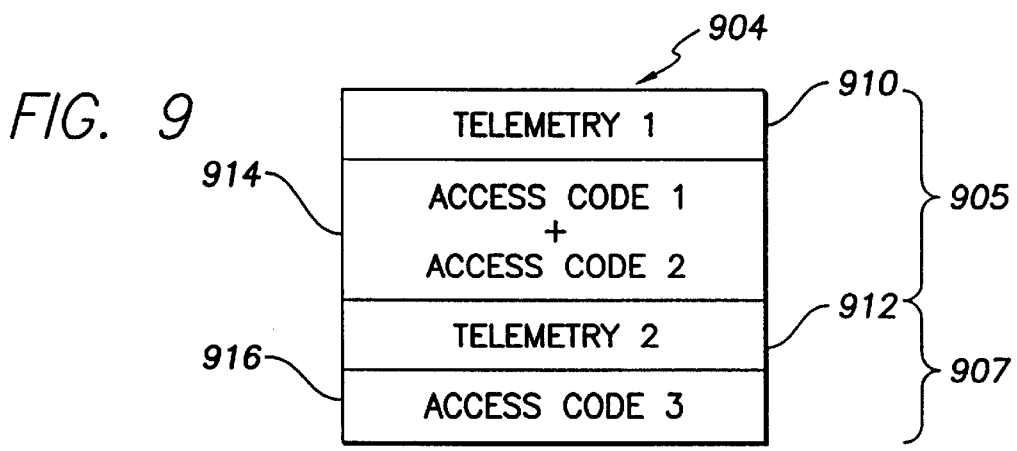
FIG. 9 shows a functional block diagram of still another telemetry circuit which may be used in the device of FIG. 1 wherein a programmer communication protocol requires two serial access codes and a non-programmer communication protocol requires one access code.

Referring now to FIG. 9, it shows another telemetry circuit 904 configured in accordance with a still further embodiment of the present invention. The telemetry circuit 904 includes a first telemetry circuit 905 and a second telemetry circuit 907. The telemetry circuits 905 and 907 each include telemetry hardware 910 and 912, respectively. The telemetry circuits 905 and 907 implement different communication protocols. To that end, the first telemetry circuit 905 has an access code control 914 which requires two serial access codes to be provided in order to establish communication with the telemetry circuit 905. On the other hand, the telemetry circuit 907 requires a single access code under control of an access code control 916.

The access code control 914 which requires successive serial access codes to be provided to gain entry may be utilized, for example, in permitting access to programmable parameters of an implantable device by a programmer. This renders the programming channel of the device more secure. In addition to the foregoing, one or both of the access codes may be modified during the communications, as for example between transmissions in a manner similar to that described previously with respect to FIG. 7. As a result, the type of external device communicating with the implantable device may be readily detected to facilitate the provision of an appropriate response. Further, by virtue of the different protocols, security is provided to the system to preclude a non-programming device from obtaining access to programmable parameters of the implantable device.

One skilled in the art will appreciate that the present invention can be practiced by other than the described embodiments, which are presented for the purpose of illustration and not of limitation, and the present invention is limited only by the claims that follows.

What is claimed is:

1. An implantable cardiac stimulation device which establishes communication with at least first and second external devices configured to communicate in accordance with first and second communication protocols, respectively, the first and second communication protocols being different, the implantable device comprising:
    a pulse generator configured to generate stimulation pulses;
    a telemetry circuit arranged to establish communication with the first and second external devices in accordance with the first and second communication protocols, respectively; and
    a control circuit coupled to the telemetry circuit and the pulse generator and further arranged to detect the first and second external devices, based on the communication protocol used by the telemetry circuit in establishing communication, and to provide a first response when the first external device is detected and a second response when the second external device is detected.

2. The device of claim 1, wherein the first and second responses are different.

3. The device of claim 1, wherein the first and second protocols are first and second encoding schemes, respectively.

4. The device of claim 1, wherein the first and second protocols are first and second data transmission rates, respectively.

5. The device of claim 1, wherein the first and second protocols include first and second access codes, respectively, the first and second access codes being different.

6. The device of claim 5, further including an access code verifier operatively coupled to the telemetry circuit that verifies, during the established communication, the access code used to establish the communication.

7. The device of claim 5, wherein the telemetry circuit is arranged to remain active during an established communication and wherein the device further includes a deactivation circuit that deactivates the telemetry circuit after completion of an established communication.

8. The device of claim 7, wherein the deactivation circuit is arranged to deactivate the telemetry circuit a predetermined time after completion of the established communication.

9. The device of claim 5, further including an access code generator operatively coupled to the telemetry circuit that changes an access code in accordance with at least one of the first and second protocols.

10. The device of claim 5, wherein an established communication includes a plurality of transmissions from a respective external device to the implantable device and wherein the implantable device includes an access code generator that changes an access code according to at least one of the protocols during an established communication.

11. The device of claim 10, wherein the access code generator is arranged to change the access code between transmissions by the respective external device.

12. The device of claim 1 further including a memory coupled to the control circuit that stores programmable parameters defining operation of the pulse generator and wherein one of the first and second responses includes access to at least some of the stored programmable parameters and the other one of the first and second responses precludes access to any of the stored programmable parameters.

13. The device of claim 1, further including a memory coupled to the control circuit, the memory including portions readable by at least one of the external devices, and wherein one of the first and second responses includes access to the readable portions of the memory.

14. The device of claim 1, further including a memory coupled to the control circuit that stores programmable parameters defining operation of the pulse generator, wherein one of the first and second responses includes access to at least some of the stored programmable parameters, and wherein a corresponding one of the first and second protocols includes first and second serial access codes.

15. The device of claim 14, wherein the first an d second access codes are different.

16. An implantable cardiac stimulation device which establishes communication with at least first and second external devices configured to communicate in accordance with first and second communication protocols, respectively, the first and second communication protocols being different, the implantable device comprising:
    pulse generating means for generating stimulation pulses;
    telemetry means for communicating with the first and second external devices in accordance with the first and second protocols; and
    control means responsive to the communication protocol of the telemetry means for detecting the first and second external devices and providing a first response upon detecting the first external device and a second response upon detecting the second external device.

17. The device of claim 16, wherein the first and second responses are different.

18. The device of claim 16 wherein the first and second protocols are first and second encoding schemes, respectively.

19. The device of claim 16, wherein the first and second protocols are first and second data transmission rates, respectively.

20. The device of claim 16, wherein the first and second protocols include first and second access codes, respectively, the first and second access codes being different.

21. The device of claim 20, further including verifying means for verifying the access code associated with at least one of the protocols during communication by the telemetry means.

22. The device of claim 20, wherein the telemetry means remains active during communication with an external device and wherein the device further includes deactivating means for deactivating the telemetry means after completion of communication with an external device.

23. The device of claim 22, wherein the deactivating means deactivates the telemetry means a predetermined time after completion of communication with an external device.

24. The device of claim 20, further including access code generating means for changing an access code in accordance with at least one of the first and second protocols.

25. The device of claim 20, wherein a communication of the telemetry means with an external device includes a plurality of transmissions between a respective external device and the telemetry means and wherein the implantable device includes access code generating means for changing an access code according to at least one of the protocols during a communication.

26. The device of claim 25, wherein the access code generating means changes the access code between transmissions by the respective external device.

27. The device of claim 16, further including memory means for storing programmable parameters defining operation of the pulse generating means and wherein one of the first and second responses includes access to at least some of the stored programmable parameters and the other one of the first and second responses precludes access to any of the stored programmable parameters.

28. The device of claim 16, further including memory means including data portions for storing data readable by at least one of the external devices, and wherein one of the first and second responses includes access to the data portions of the memory.

29. The device of claim 16, further including a memory means for storing programmable parameters defining operation of the pulse generating means, wherein one of the first and second responses includes access to at least some of the stored programmable parameters, and wherein a corresponding one of the first and second protocols includes first and second serial access codes.

30. The device of claim 29, wherein the first and second access codes are different.

31. In an implantable cardiac stimulation device which provides therapy to a heart, a method of communicating with at least first and second external devices configured to communicate in accordance first and second communication protocols, respectively, the first and second protocols being different, the method including the steps of:
    communicating with one of the first and second external devices with one of the first and second protocols corresponding to one of the first and second external devices;
    detecting the one of the first and second external devices based upon the protocol used to communicate with the one of the external devices; and
    selecting a response among first and second responses, the first response corresponding to detection of the first external device and the second response corresponding to detection of the second external device.

32. The method of claim 31, wherein the first and second responses of the selecting step are different.

33. The method of claim 31, wherein the first and second protocols of the communicating step are first and second encoding schemes, respectively.

34. The method of claim 31, wherein the first and second protocols of the communication step are first and second data transmission rates, respectively.

35. The method of claim 31, wherein the first and second protocols of the communicating step include first and second access codes, respectively, the first and second access codes being different.

36. The method of claim 35, further including the step of verifying the address code associated with at least one of the protocols during the communicating step.

37. The method of claim 35, wherein the communicating step includes maintaining a communication channel active during communication with the one of the first and second external devices and wherein the method further includes the step of the deactivating the communication channel after completion of the communicating step.

38. The method of claim 37, wherein the deactivating step is performed a predetermined time after completion of the communicating step.

39. The method of claim 35, further including the step of changing an access code in accordance with the one of the first and second protocols during the communicating step.

40. The method of claim 35, wherein the communicating step includes a plurality of transmissions between the one of the first and second external devices and the implantable device and wherein the communicating step further includes the step of changing an access code according to the one of the protocols after selected transmissions.

41. The method of claim 40, wherein the access code changing step is performed between each transmission.

42. The method of claim 31, further including the step of storing programmable therapy defining parameters in a memory and wherein one of the first and second responses includes permitting access to at least some of the stored programmable parameters and the other one of the first and second responses includes precluding access to any of the stored programmable therapy defining parameters.

43. The method of claim 31, further including the step of storing data readable by at least one of the external devices in data portions of a memory, and wherein one of the first and second responses includes permitting access to the data portions of the memory.

44. The method device of claim 31, further including the step of storing programmable therapy defining parameters in a memory, wherein one of the first and second responses includes permitting access to at least some of the stored programmable therapy defining parameters, and wherein a corresponding one of the first and second protocols includes first and second serial access codes.

45. The method of claim 44, wherein the first and second access codes are different.

\* \* \* \* \*